United States Patent [19]

Apkarian

[11] Plant 5,241

[45] Jun. 5, 1984

[54] NECTARINE TREE NAMED 'AMA LIN'

[75] Inventor: Vartan T. Apkarian, 8031 S. Crawford, Reedley, Calif. 93654

[73] Assignees: Vartan T. Apkarian; Donald K. Ninkovich; Betty Apkarian, all of Reedley, Calif.

[21] Appl. No.: 450,113

[22] Filed: Dec. 15, 1982

[51] Int. Cl.[3] ..... A01H 5/00

[52] U.S. Cl. ..... Plt./41

[58] Field of Search ..... Plt./41

*Primary Examiner*—James R. Feyrer

*Attorney, Agent, or Firm*—Huebner & Worrel

[57] ABSTRACT

A nectarine tree generally similar to the May Grand Nectarine Tree (U.S. Plant Pat. No. 2,794) and bearing yellow fleshed, semi-freestone fruit which ripens about eight days earlier than the fruit of the May Grand, which has a substantially fully red coloration and is even ripening, and which is of uniform, symmetrical, and substantially spherical form.

1 Drawing Figure

BACKGROUND OF THE NEW VARIETY

The present invention relates to a new and distinct variety of nectarine tree generally similar to the May Grand Nectarine Tree (U.S. Plant Pat. No. 2,794) of which it is a sport. The May Grand is an important variety of commercially planted nectarine tree since its fruit is relatively early ripening, is of good size and symmetrical form, and has a substantially completely red skin coloration. There are other varieties of nectarines, such as the Aurelia, which bear fruit ripening even earlier than the fruit of the May Grand variety, but such very early ripening varieties, typically, are of small size and unsymmetrical form and have a coloration inferior to that of the May Grand. There is a period between the ripening of such very early ripening varieties and the ripening of the May Grand variety during which the fruit of no commercially well-known variety of nectarine tree is ready for harvest. Early ripening nectarines have, in general, a tendency to produce soft tips due to uneven ripening, such tips being easily damaged in shipping.

As with other fresh produce, the time of harvest of nectarines greatly influences the price they bring on the market. Generally, if a fruit ripens early, or otherwise ripens when other fruits of the same variety are not available, the higher the price if the fruit has other desirable characteristics. Three desirable characteristics in fresh fruits are large size; bright and attractive coloration; and symmetrical form. A fourth desirable characteristic is uniformity between fruits in size, coloration and form. As a result, most desirable varieties of nectarines are those which are, for their ripening season, of large size, attractive coloration, and globular form. It is evident, therefore, that a variety of nectarine tree which bears fruit having these characteristics and which ripens in the period between the ripening of the earliest ripening nectarine varieties and the ripening of the May Grand variety, would be highly desirable.

ORIGIN AND ASEXUAL REPRODUCTION OF THE NEW VARIETY

The new variety of nectarine tree was discovered by me as a sport of a tree growing in an orchard of May Grand nectarine trees planted in 1963, said orchard being included in a ranch, designated Ranch No. 12, located on the northeast corner of Navelencia and South Avenues, near the City of Reedley, in the County of Fresno, in the State of California, said ranch being owned and operated by a partnership of which I am a general partner. In 1977, I asexually reproduced the sport by grafting it onto a Springcrest Peach Tree, (a variety developed by the U.S. Department of Agriculture), located on a ranch, also owned and operated by the partnership referred to above and designated as Ranch No. 11, located on the south side of South Avenue, one-eighth of a mile west of Crawford Avenue near the City of Reedley, County of Fresno, in the State of California. The resulting tree was carefully observed for a period of three years and it was found that the fruit and tree characteristics resulting from such graft proved identical to those of the original sport.

In 1979, during the designated period of three years, said partnership contracted with others to reproduce asexually the new variety by grafting over 1,000 buds thereof onto seedling rootstock, variety unknown, and the resulting trees were planted on a ranch, designated as Ranch No. 10, a third ranch owned and operated by the partnership referred to and located on the southwest corner of Lincoln and Alta Avenues near the same city. Fruit from such resulting trees was first harvested in May 1982.

SUMMARY OF THE NEW VARIETY

The instant variety of nectarine tree is characterized by its general resemblance to the May Grand variety of nectarine tree (U.S. Plant Pat. No. 2,794), of which the new variety is a sport, in bearing fruit which is relatively early ripening and which has an overall red skin coloration. The new variety has the important distinction from the May Grand in that the fruit of the instant variety ripens about eight days earlier than the fruit of an ungirdled nectarine tree of the May Grand variety and of ripening three to five days earlier than a girdled tree of such variety. This ripening of the new variety is during a hiatus between ripening of the fruit of the very early ripening varieties of nectarines, such as the Aurelia variety, which compare unfavorably with the May Grand variety from the standpoints of size, uniformity, and coloration and the ripening of the fruit of the May Grand variety. The fruit of the instant variety is further characterized by being of uniform size and being of very large size for its ripening period; by having a full and deep red skin coloration; by being uniformly of substantially spherical form; and by ripening evenly, the fruit of the new variety having generally yellow flesh, being semi-freestone, and by having desirable eating and shipping qualities.

BRIEF DESCRIPTION OF THE DRAWING

The accompanying drawing is a color photograph of mature nectarines of the subject variety, together with a typical twig showing characteristic leaves, two of the nectarines being divided to show the flesh color along the suture plane.

DETAILED DESCRIPTION

Referring more specifically to the pomological details of the new distinct variety of nectarine tree, the following have been observed under the ecological conditions prevailing at the above-designated Ranch No. 10, the fruit being described in a condition after the fruit was harvested at the stated time of maturity and subsequently maintained in cold storage for about thirty days. The color code plate identifications are by reference to the Maerz and Paul, *Dictionary of Color,* (New York, McGraw-Hill, 1950), other color names being common descriptive names.

TREE

Size: Above average size for a nectarine tree.
Productivity: Good.
Leaves:
- *Length.*—80 To 170 mm, average 150 mm.
- *Width.*—20 To 40 mm, average 35 mm.
- *Shape.*—Lanceolate, apex acuminate.
- *Color.*—Upperside 23-L-8; Underside 21-H-5.
- *Marginal form.*—Shallowly serrulate, nearly crenate.
- *Petiole.*—Average length 10 mm, average thickness 2 mm.
- *Glandular charcteristics.*—Three to six in number, usually two on base of leaf blade, one to four on petiole, reniform.
- *Stipules.*—Most leaves exstipulate, occasional leaves have a single stipule which is dark reddish-brown in color and is 4 to 6 mm in length.

FLOWERS

Smaller and darker in color than blossoms of May Grand Nectarine Tree (U.S. Plant Pat. No. 2,794).

FRUIT

Maturity: About eight days before ungirdled May Grand and three to five days before girdled May Grand, following Aurelia.
Size: Large for early ripening season, uniform.
- *Diameters.*—Axial, transverse in suture plane, and transverse at right angles to suture plane each 58–68 mm, average 65 mm, dependent on cultural conditions.

Form: Uniformly globose and symmetrical, substantially spherical.
- *Suture.*—Very shallow, often only distinguishable by skin coloration; extends along entire ventral side; slight depression beyond pistil point; occasionally distinguishable on dorsal side.
- *Ventral surface.*—Rounded.
- *Stem cavity.*—Average: 20 mm width, 30 mm length, 15 mm depth; often splotched with yellow, about 11-L-2 (Pyrethrum Yellow).
- *Base.*—Flattened.
- *Apex.*—Rounded.
- *Pistil point.*—Acuminate, occasionally slight.
- *Stem caliper.*—3 To 4 mm.

Skin:
- *Thickness.*—Medium.
- *Tendency to crack.*—None observed.
- *Pubescence.*—None.
- *Color.*—Nearly solid red, from 4-J-11 (Canna Antique Red) to 7-L-7 (Maroon), often with minute spots or, occasionally, splotches of yellow, about 9-I-5.

Flesh:
- *Color.*—Pit cavity surface and adjacent flesh yellow, 9-I-2 darkening toward skin to an orange hue, 10-L-8; between pit cavity and skin there are minute reddish streaks and spots, about 4-L-3.
- *Amygdalin.*—Wanting.
- *Juice.*—Moderately juicy.
- *Flavor.*—Excellent, sweet and subacid.
- *Aroma.*—Mild but distinct.
- *Texture.*—Medium firm.
- *Fibers.*—None.
- *Ripening.*—Even.
- *Eating quality.*—Excellent.

Stone: Semi-free, adheres to flesh but flesh separates cleanly from stone when sufficient force is applied.
- *Fibers.*—None.
- *Size.*—Axial length, 30–35 mm; width in suture plane 25 mm average; total width at right angle to suture plane, 18 mm average.
- *Apex.*—Bears acuminate point.
- *Sides.*—Equal.
- *Grooves.*—Ventral grooves: extend from base about two-thirds of distance to apex, usually symmetrical; dorsal grooves: shallow, extend from base to apex.
- *Splitting tendency.*—None.

Use: Fresh market.
- *Shipping quality: Excellent.*

Keeping quality: Good.

Although the new variety of nectarine tree possesses the described characteristics as a result of growing conditions in Fresno County, Calif., in the central part of the San Joaquin Valley, it is to be understood that variations of the usual magnitude in characteristics incident to growing conditions, fertilization, pruning and pest control are to be expected.

Having thus described and illustrated my new variety of nectarine tree, I claim:

1. A new and distinct variety of nectarine tree, substantially as illustrated and described, characterized by its bearing of semi-freestone, yellow fleshed, even ripening fruit having a full and dark red skin coloration, being uniformly of large size for its early ripening period, and being uniformly of substantially spherical form and being particularly characterized by bearing such fruit about eight days earlier than an ungirdled tree of the May Grand variety (U.S. Plant Pat. No. 2,794) bears fruit.

* * * * *

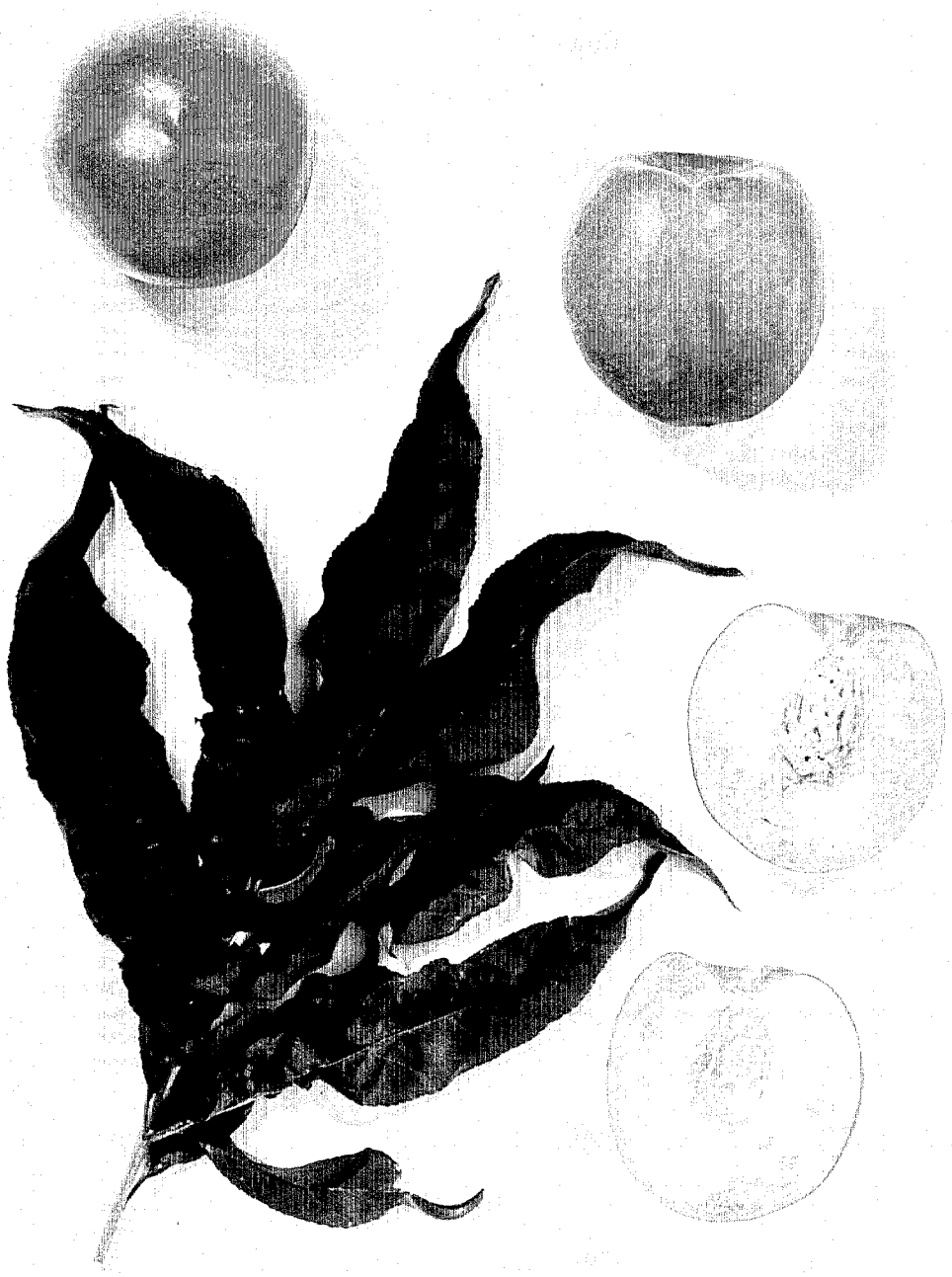

UNITED STATES PATENT AND TRADEMARK OFFICE

CERTIFICATE OF CORRECTION

PATENT NO. : PP 5,241

DATED : June 5, 1984

INVENTOR(S) : Vartan T. Apkarian

It is certified that error appears in the above-identified patent and that said Letters Patent is hereby corrected as shown below:

On the title page:
Column 1, [73], after "Betty Apkarian", insert --- Thomas V. Apkarian, Sue Ann Apkarian, Donna Ninkovich-Apkarian, Robert S. Poochigian and Nancy J. Poochigian, doing business as T. Apkarian & Sons ---.

Signed and Sealed this

Fifth Day of March 1985

[SEAL]

*Attest:*

DONALD J. QUIGG

*Attesting Officer* *Acting Commissioner of Patents and Trademarks*